United States Patent [19]

Leidig

[11] B 4,014,938

[45] Mar. 29, 1977

[54] 4-TRICYCLO[5,2,1,0$^{2,6}$]DECYL-8-BUTANAL

[75] Inventor: Theodor Leidig, Holzminden, Germany

[73] Assignee: Haarmann & Reimer GmbH, Holzminden, Germany

[22] Filed: Nov. 18, 1974

[21] Appl. No.: 524,849

[44] Published under the second Trial Voluntary Protest Program on March 23, 1976 as document No. B 524,849.

[30] Foreign Application Priority Data

Nov. 30, 1973 Germany .......................... 2359659

[52] U.S. Cl. ........................... 260/598; 260/611 F; 252/522

[51] Int. Cl.$^2$ ........................................ C07C 47/30

[58] Field of Search ..................................... 260/598

[56] References Cited

UNITED STATES PATENTS

| | | | |
|---|---|---|---|
| 2,817,673 | 12/1957 | Roelen et al. | 260/598 X |
| 2,875,244 | 2/1959 | Bartlett et al. | 260/598 X |
| 3,786,075 | 1/1974 | Telsseire et al. | 260/611 F |

*Primary Examiner*—Bernard Helfin
*Attorney, Agent, or Firm*—Burgess, Dinklage & Sprung

[57] ABSTRACT

The invention concerns the new tricyclic compound, 4-(tricyclo [5.2.1.0$^{2,6}$] decyl-8)-butanal, a process for its preparation and its use as a perfume.

1 Claim, No Drawings

4-TRICYCLO[5,2,1,0$^{2,6}$]DECYL-8-BUTANAL

The invention relates to a new tricyclic compound, 4-(tricyclo [5,2,1,0$^{2,6}$] decyl-8)-butanal, a process for its preparation and to its use as a perfume.

The process for the preparation of 4-(tricyclo [5,2,1,0$^{2,6}$]decyl-8)-butanal comprising:
a. reacting tricyclo [5,2,1,0$^{2,6}$] decanone-8 with 1-methoxy-buten-1-ine-3 in the presence of a basic catalyst to form 1-methoxy-4-(8-hydroxytricyclo [5,2,1,0$^{2,6}$] decyl-8)-buten 1-ine-3 as condensation product;
b. selectively hydrogenating on the triple bond the condensation product of step (a);
c. subjecting the product of step (b) to ether splitting in the presence of an acid catalst to result in dehydration accompanied by the formation of 4-(tricyclo [5,2,1,0$^{2,6}$] decylidene-8)-buten-2-al-1;
d. converting the buten-2-al-1 derivative of step (c) into 4-(tricyclo [5,2,1,0$^{2,6}$] decyl-8)-butanal by complete hydrogenation of the double bonds.

Tricyclo [5,2,1,0$^{2,6}$] decanone-8 is already known (see e.g. Beilsteins Handbuch der org. Chemie, 4th Edition, Vol 7, 2nd Supplementary Volume, page 133). 1-Methoxy-buten-1-ine-3 is prepared analoguous to the process described in the German patent specification 601 822 for the preparation of 1-alkoxy-buten-1-ines-3.

In the first stage (a) of the process according to the invention, the starting components tricyclo [5,2,1,0$^{2,6}$]decanone-8 and 1-methoxy-buten-1-ine-3 are generally used in equimolar quantities although in order to obtain an increased yield it may be advantageous to use one of the two reactants in an excess up to 0.2 mol, the compound used in excess being preferably tricyclo-decanone-8 since this can be recovered more easily from the reaction mixture.

The process according to the invention may be carried out, by condensing in the first reaction stage (a) the starting materials tricyclo [5,2,1,0$^{2,6}$] decanone-8 and 1-methoxy-buten-1-ine-3 in conventional manner in an inert solvent, e.g. a hydrocarbon such as cyclohexane or a light petroleum fraction in the presence of a strongly basic catalyst such as sodamide or potassium hydroxide, generally employing reaction temperatures e.g. of 0° to 45°C, preferably 5° to 20°C, and reaction times generally between about 6 and 24 hours. The product is obtained in the form of a salt and is converted into 1-methoxy-4-(8-hydroxy-tricyclo[5,2,1,0$^{2,6}$] decyl-8)-buten-1-ine-3 by reacting it with acid, e.g. glacial acetic acid, in conventional manner.

As basic catalysts there are mentioned especially strongly basic catalysts such as alkali hydroxides, e.g. sodium and potassium hydroxide; or alkalamides, e.g. sodamide; or alkali alcoholates, e.g. sodium methylate and sodium ethylate.

In the second reaction stage(b), 1-methoxy-4-(8-hydroxy-tricyclo [5,2,1,0$^{2,6}$] decyl-8)-buten-1-ine-3 is partially hydrogenated in the presence of a catalyst which is selective for triple bonds. Hydrogenation is carried out in conventional manner, e.g. in the presence of a Lindlar-catalyst. A solvent may be used which is inert under these reaction conditions, e.g. tetrahydrofuran, methanol, ethanol, cyclohexane, ether or ethyl acetate. Hydrogenation may be carried out e.g. at temperatures of from 0° to 120°C, preferably from 20° to 40°C.

After having removed the catalyst, the product obtained in the second reaction stage (b) is subjected in the third reaction stage (c) to ether splitting and dehydration by heating in the presence of an acid catalyst whereby is obtained as reaction product 4-(tricyclo [5,2,1,0$^{2,6}$] decylidene-8)-buten-2-al-1. Ether splitting may be carried out e.g. at a temperature of from 100°C to 150°C and under a vacuum of 100 to 200 mm Hg.

As acid cytalysts for ether splitting and dehydration there are mentioned for example: inorganic or organic proton acids, such as hydrochloric acid, sulfuric acid, phosphoric acid, p-toluenesulphonic acid, adipic acid and trifluoro acetic acid; or Lewis acids such as aluminium chloride, ferric-chloride and boronfluoride-etherate, or acid ion exchangers, such as montmorillonites, glauconites or zeolites.

In the fourth reaction stage (d), the product obtained from ether splitting is converted into the desired tricyclo [5,2,1,0$^{2,6}$] decyl-8-butanal by complete hydrogenation of the double bonds. Hydrogenation may be carried out e.g. on a palladium catalyst in the presence of solvents such as tetrahydrofuran, methanol, ethanol, cyclohexane, ether or ethyl acetate.

The individual reaction stages of the process according to the invention may be represented by the following reaction scheme:

1st Stage:

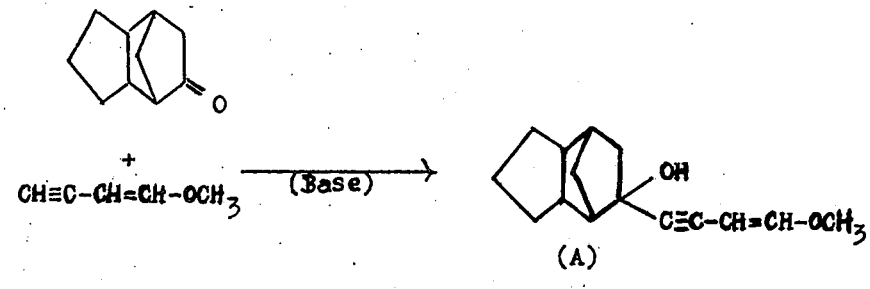

2nd Stage:

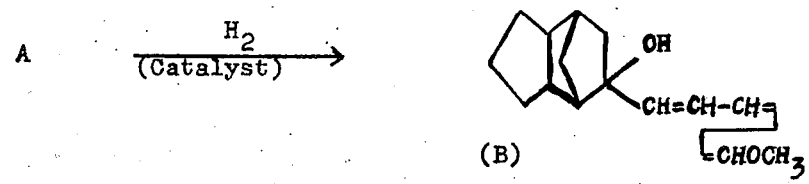

3rd Stage:

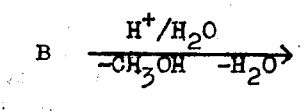 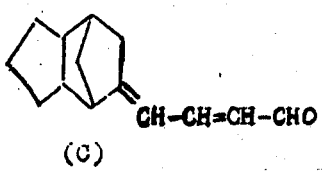
(C)

4th Stage:

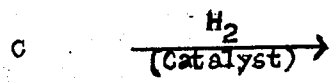 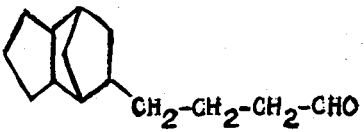

4-(Tricyclo [5,2,1,0$^{2,6}$] decyl-8)-butanal is a perfume with novel properties. It has floral, creamy-waxy characteristics reminiscent of nuances of the perfume of lily of the valley and pollen and spicy characteristics reminiscent of nuances of honeysuckle. It is eminently suitable for use as a single perfume or as component of perfume compositions. It is suitable for scenting finished products such as cosmetics, soaps, soap powders, detergents, toilet water, lotions, aerosols, creams and powders. The compound according to the invention should generally be present in these products in quantities of over 0.1 % by weight and preferably over 1 % by weight refered to the weight of the finished products.

The reproduction of the floral, creamy-waxy and spicy perfume nuances with the aid of the odoriferous complex of a single perfume opens up new technical possibilities to impart "fullness" and exceptional originality to a perfume or a perfume composition.

The 1-methoxy-4-(8-hydroxy-tricyclo [5,2,1,0$^{2,6}$] decyl-8-buten-1-ine-3 formed in the first reaction stage (a) is a new compound which constitutes a valuable intermediate product for the preparation of perfumes containing a tricyclo [5,2,1,0$^{2,6}$]decyl-8-residue.

Another object of this invention is therfore 1-methoxy-4-(8-hydroxy-tricyclo [5,2,1,0$^{2,6}$] decyl-8)-buten-1-ine-3, the method for its preparation and its use for the preparation of perfumes containing a tricyclo [5,2,1,0$^{2,6}$] decyl-8-residue.

The invention is illustrated by the following examples.

EXAMPLE 1 a. Preparation of 1-methoxy-4-(1-hydroxy-tricyclo[5,2,1,0$^{2,6}$]decyl-8)-buten-1-ine-3.

30 l of benzene were introduced into a stirrer vessel equipped with a stirrer, a feed device and cooling means, and 3.6 kg (90 mol) of sodamide were suspended therein with stirring. The suspension was cooled to 10°C and a mixture of 15 kg of tricyclo [5,2,1,0$^{2,6}$] decanone-8 and 7.50 kg of methoxy butenine was slowly added during a period of 12 hours. Stirring was then continued for a further 12 hours, the reaction temperature being maintained at about 10°C during the entire reaction time by cooling. The solution in benzene was then poured into a mixture of 12 kg of glacial acetic acid and 50 kg of ice. The benzene phase was then separated and washed with water and saturated bicarbonate solution. The benzene was evaporated off and the product was subjected to fractional distillation under vacuum. 15.40 kg of pure 1-methoxy-4-(8-hydroxy-tricyclo[5,2,1,0$^{2,6}$]decyl-8)-buten-1-ine-3 (about 72% based on the methoxybutenine put into the reaction) were obtained from the fraction which distilled off between 180° and 184°C at 3 mm Hg.

b. Partial hydrogenation of 1-methoxy-4-(8-hydroxy-tricyclo [5,2,1,0$^{2,6}$]-decyl-8)-buten-1-ine-3

5 mol = 1.16 kg of 1-methoxy-4-(8-hydroxy-tricyclo[5,2,1,0$^{2,6}$]decyl-8)-buten-1-ine-3 were filled up with tetrahydrofuran and hydrogenated with 5 g of Lindlar catalyst in a 5 l autoclave at room temperature until 5 mol of H$_2$ had been taken up.

After removal of the catalyst and evaporation of the solvent by means of a thin layer evaporator, the hyrogenation product was immediately subjected to ether splitting without redistillation (crude product approximately 1.10 kg).

c. Ether splitting of the hydrogenation product

1% by weight of p-toluenesulphonic acid was added to the hydrogenation product which had been freed from catalyst and solvent, and the mixture of hydrogenation product and p-toluenesulphonic acid was heated to 120°C under a vacuum of 100 to 200 mm Hg until no more methanol distilled off. After completion of the reaction, the product obtained was distilled under a vacuum of 2 mm Hg.

The crude product which was obtained in a yield of about 60 % contained 90 % of 4-(tricyclo [5,2,1,0$^{2,6}$] decylidene-8)-buten-2-al-1.

B.p. : 156°–170°C/2 mm Hg
D$_4^{20}$ : 1.037
n$_D^{20}$ : 1. 5830
λ max : 296 mu
ε : 2600 d. Hydrogenation of tricyclo [5,2,1,0$^{2,6}$] decyl-8-butanal

The crude 4-(tricyclo [5,2,1,0$^{2,6}$] decylidene-8)-buten-2-al-1 from Example 1c was mixed with an equal volume of tetrahydrofuran and hydrogenated with 1 g of 10 % palladium on charcoal per mol of starting material at room temperature until no more hydrogen was taken up. When freed from solvent and catalyst, the resulting product was distilled under vacuum.

B.p. : 107°–111°C/0.9 mm Hg
$D_4^{20}$ : 1.000
$n_D^{20}$ : 1.4987
Yield: quantitative The product obtained had a novel scent complex with a floral creamy-waxy characteristic reminiscent of lily of the valley and pollen and a spicy characteristic reminiscent of honeysuckle.

EXAMPLE 2

Example for the use of tricyclo[5,2,1,0$^{2,6}$] decyl-8-butanal in a perfume composition with the character of honeysuckle:

```
   2 isoeugenol
  10 isoeguenol-methyl ether
   5 guaiacol oil
  50 guajyl acetate
  40 cananga oil
  10 marjoram oil
  50 myrcenyl acetate
  40 linalyl acetate
  80 rose wood oil, bras.
  35 terpineol
  10 α-ionone
  50 phenyl ethyl-dimethyl-carbinol
  25 phenyl ethyl acetate
 100 phenyl ethyl alcohol
  50 geraniol
  23 citronellol
 150 farnesol
 120 hydroxycitronellal
 150 tricyclo[5,2,1,0²,⁶]decyl-8-butanal
1000 parts by weight.
```

This honeysuckle perfume has an unharmonious, synthetic, chemical character without the tricyclo[5,2,1,0$^{2,6}$]decyl-8-butanal but when this compound is added the spicy and floral odours are pleasantly combined as in natural honeysuckle.

EXAMPLE 3

Example for the use of tricyclo[5,2,1,0$^{2,6}$]decyl-8-butanal in a perfume composition with the character of lily of the valley

```
   2 10% solution of cis-hexanol in diethyl phthalate
  20 decyl acetate
  60 terpineol
 120 geraniol
  50 citronellol-1
  58 citronellol
  40 geranyl acetate
  95 phenyl ethyl alcohol
  20 10% solution of cis jasmone in diethyl phthalate
  25 α-amyl-cinnamaldehyde
  10 African geranium oil
  60 Nerolidol
  30 cabreuva oil
  10 cinnamyl alcohol
 400 tricyclo[5,2,1,0²,⁶]decyl-8-butanal
1000 Parts by weight
```

The odour of the lily of the valley perfume is "empty" simple and artificial without tricyclo[5,2,1,0$^{2,6}$]decyl-8-butanal, but the addition of this compound imparts to the perfume a floral, creamy fullness which renders it substantially more suitable for use in cosmetics.

I claim:
1. 4-Tricyclo [5,2,1,0$^{2,6}$] decyl-8-butanal.

* * * * *